United States Patent [19]

Maki

[11] 4,172,946

[45] Oct. 30, 1979

[54] METHOD FOR MANUFACTURE OF FLUOROALKYL PYRIDINES

[75] Inventor: Yasuo Maki, Nagoya, Japan

[73] Assignee: Agency of Industrial Science and Technology, Ministry of International Trade & Industry, Tokyo, Japan

[21] Appl. No.: 965,188

[22] Filed: Nov. 30, 1978

[30] Foreign Application Priority Data

Dec. 7, 1977 [JP] Japan .................................. 52-146758

[51] Int. Cl.$^2$ .......................................... C07D 213/26
[52] U.S. Cl. ................................................... 546/346
[58] Field of Search .......................................... 546/346

[56] References Cited

U.S. PATENT DOCUMENTS

| | | | |
|---|---|---|---|
| 4,038,331 | 7/1977 | Tobin | 260/651 F |
| 4,101,554 | 7/1978 | Tobin | 546/346 |

OTHER PUBLICATIONS

Yagupol'ski et al., J. Gen. Chem., U.S.S.R., vol. 38, pp. 644, 1692, (1968).

*Primary Examiner*—Alan L. Rotman
*Attorney, Agent, or Firm*—Kurt Kelman

[57] ABSTRACT

Fluoroalkyl pyridines are produced in high yields by causing pyridines to react with fluoroalkyl iodides in the atmosphere of ammonia gas.

3 Claims, No Drawings

METHOD FOR MANUFACTURE OF FLUOROALKYL PYRIDINES

BACKGROUND OF THE INVENTION

This invention relates to a method for the manufacture of fluoroalkyl pyridines useful as raw material for the production of surface active agents. More particularly, this invention relates to a method for the manufacture of fluoroalkyl pyridines represented by the general formula:

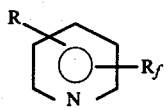

(wherein, R denotes a hydrogen atom or a methyl group and $R_f$ a chain fluoroalkyl group having from one to ten carbon atoms). Regarding the manufacture of fluoroalkyl pyridines, there has heretofore been known a method for obtaining heptafluoropropyl pyridine by heating a pyridine and heptafluoropropyl iodide in a sealed tube at 185° C. [L. M. Yagupol'skii, A. G. Galushko, M. A. Rzhavinskaya; Zh. Obsh. Khim 38 668 (1968)]. By this method, however, the reaction entails occurrence of a large amount of tarry by-product and the separation of the reaction product in a purified form from the reaction mixture is extremely difficult. If a fluoroalkyl iodide other than the heptafluoropropyl iodide is used in the reaction with the pyridine, the corresponding fluoroalkyl pyridine is obtained in a yield too low to render the manufacture commercially feasible.

The object of the present invention is to provide a method for the manufacture of fluoroalkyl pyridines in high yields from pyridines and fluoroalkyl iodides, which method entails no or little occurrence of by-product and, therefore, permits ready purification of the reaction product.

SUMMARY OF THE INVENTION

To accomplish this object, the inventor made various studies and has, consequently, discovered that the reaction of various fluoroalkyl iodides having from one to ten carbon atoms with pyridines, when carried out in the atmosphere of ammonia gas, produces corresponding fluoroalkyl pyridines in high yields and that the method proceeds while repressing occurrence of a tarry by-product and permits easy separation of the desired reaction product in a pure state.

DETAILED DESCRIPTION OF THE INVENTION

This invention aims to manufacture, in one stage, a fluoroalkyl pyridine of General Formula (1) by heating in the atmosphere of ammonia gas a mixture consisting of a pyridine and a fluoroalkyl iodide. The reaction involved in this manufacture is represented by the following chemical formula:

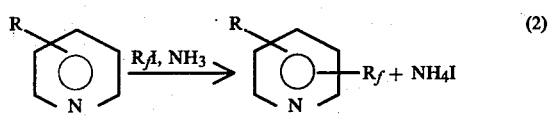

The reaction of the fluoroalkyl iodide with the pyridine entails liberation of hydrogen iodide. This hydrogen iodide ordinarily causes a reductive deiodization with respect to the fluoroalkyl iodide and functions to promote harmful secondary reactions such as the formation of dipyridyl with reference to the pyridine. In the present invention, however, since the reaction is carried out in the atmosphere of ammonia gas, the ammonia gas is combined with the hydrogen iodide to give rise to ammonium iodide, thus enabling the harmful hydrogen iodide to be eliminated very easily.

Since the reaction of the present invention is carried out by heating the reactants in the atmosphere of ammonia gas, the vessel used for this reaction is required to possess a pressureproof construction.

Examples of pyridines which are usable as one of the raw materials include of pyridine, α-methyl pyridine, β-methyl pyridine, γ-methyl pyridine and the like. At least one of these pyridines is used. Fluoroalkyl iodides which are usable as the other raw material include those having from one to ten carbon atoms. Typical examples include trifluoromethyl iodide, pentafluoroethyl iodide, 1-iodo-heptafluoro-n-propane, 1-iodo-perfluoro-n-hexane, 1-iodo-perfluoro-n-heptane and 1-iodo-perfluoro-n-decane.

The mixing ratio of the fluoroalkyl iodide to the pyridine is from 0.1 to 0.4 mol of the former to 1 mol of the latter. This range of the mixing ratio is critical: If the amount of the fluoroakyl iodide is less than 0.1 mol per mol of pyridine, the amount of the corresponding fluoroalkyl pyridine to be produced in one operation is too small to make the manufacture commercially feasible, although the reaction proceeds without hindrance. If the amount of the fluoroalkyl iodide exceeds 0.4 mol per mol of pyridine, the amount of the hydrogen iodide which is consequently liberated in the reaction increases excessively relative to that of the ammonia gas, to the extent of obstructing smooth progress of the reaction.

Preferably the mixing ratio is from 0.12 mol to 0.20 mol of the fluoroalkyl iodide to 1 mol of the pyridine. The ammonia is introduced in a gaseous form into the reaction vessel containing therein the mixture of the reactants. At this time, the reaction vessel is maintained at temperatures in the range of from 0° C. to 5° C. The maintenance of the vessel in this temperature range may be advantageously accomplished by cooling with ice.

The amount of ammonia thus introduced into the reaction vessel must be at least an equivalent mol relative to the amount of the fluoroalkyl iodide being used in the reaction. After the introduction of the ammonia, the reaction vessel is sealed airtightly and heated to induce the reaction. The heating of the reaction system is performed at temperatures in the range of from 175° C. to 190° C. for a period of from three hours to 24 hours. The reason for the wide range of heating temperature and time is that, generally, the shorter the length of the carbon chain of the fluoroalkyl iodide the less readily the reaction proceeds so that the heating temperature and time must be increased.

After the reaction, the fluoroalkyl pyridine aimed at is extracted from the reaction mixture with hexane, the hexane layer is washed with an aqueous 5% acetic acid solution or an aqueous 3% hydrochloric acid solution to expel the unaltered pyridine and the washed hexane layer is distilled. The fluoroalkyl pyridine thus obtained by the reaction is a colorless liquid or solid emitting a weak odor of pyridine.

When the fluoroalkyl pyridine is manufactured by the method of this invention, the reaction involved therein proceeds without entailing any appreciable occurrence of by-products because it is carried out in the atmosphere of ammonia gas. Thus, the product by this invention is obtained in yields as high as 60% or more, whereas in the reaction carried out in the absence of ammonia gas, the product is obtained generally in low yields of from 20 to 30%. Moreover, the product permits extremely easy purification. Thus, the product can be easily obtained in an extremely high purity exceeding 99%.

Now, the present invention will be described specifically with reference to working examples and referential examples cited herein below by way of illustration of the advantage of the present invention.

EXAMPLE 1

In a reaction vessel having an inner volume of 100 cc and proofed against resistance of 20 kg, 15.82 g (0.20 mol) of pyridine and 7.83 g (0.04 mol) of trifluoromethyl iodide were mixed. With the vessel cooled with ice (to about 5° C.), ammonia gas was introduced into the vessel at a rate of 60 ml per minute for five minutes. Then, the vessel was airtightly sealed and heated at 180° C. for 24 hours. After the reaction, the vessel was cooled to room temperature and the reaction mixture was removed from the cooled vessel. The reaction mixture was combined with 15 ml of water and the desired product was extracted with 20 ml of hexane twice. The resultant extract was washed with an aqueous 5% acetic acid solution until the washing assumed acidity. The washed extract was washed with water and dried over anhydrous sodium sulfate and then distilled. Trifluoromethyl pyridine was distilled at 125° to 140° C. to a total amount of 3.55 g (60.4% of theoretical value). The mixing ratio of the isomers $\alpha:\beta:\gamma$ was 46:40:13.

EXAMPLE 2

In the same reaction vessel as used in Example 1, 18.62 g (0.20 mol) of $\gamma$-methyl pyridine and 7.39 g (0.025 mol) of 1-iodo-heptafluoro-n-propane were mixed. Similarly to Example 1, ammonia gas was introduced into to reaction vessel at the rate of 60 ml per minute for five minutes. Then, the reaction vessel was airtightly sealed and heated at 180° C. for six hours. After the reaction, the reaction mixture was combined with 10 ml of water and the desired product was extracted with 20 ml of hexane twice. The extract was washed with an aqueous 3% hydrochloric acid solution until the washing assumed acidity. The washed extract was washed with water and then dried and distilled in the same way as in Example 1. Heptafluoro-n-propyl-$\gamma$-methyl-pyridine was distilled at 75°–85° C./40 mmHg to a total amount of 3.96 g (60.7% of theoretical value). This product was found to be a 70:30 mixture of $\alpha$-$R_f$ and $\beta$-$R_f$ isomers.

EXAMPLE 3

In the same reaction vessel as used in Example 1, 15.82 g (0.20 mol) of pyridine and 12.48 g (0.028 mol) of 1-iodo-perfluoro-n-hexane were mixed and the mixture was treated by following the procedure of Example 2. Perfluoro-n-hexyl pyridine was distilled at 90°–94° C./19 mmHg to a total amount of 8.86 g (79.8% of theoretical value). The mixing ratio of the isomers $\alpha:\beta:\gamma$ was 45:41:13.

EXAMPLE 4

In the same reaction vessel as used in Example 1, 18.62 g (0.20 mol) of $\beta$-methyl pyridine and 7.62 g (0.031 mol) of pentafluoroethyl iodide were mixed and the mixture was treated in the same manner as in Example 1. Pentafluoroethyl-$\beta$-methyl pyridine was distilled at 71°–75° C./30 mmHg to a total amount of 4.45 g (68.1% of theoretical value). This substance was found to be a 36:8:20:36 mixture of 2-$R_f$, 4-$R_f$, 5-$R_f$ and 6-$R_f$ isomers.

EXAMPLE 5

In the same reaction vessel as used in Example 1, 18.62 g (0.20 mol) of $\gamma$-methyl pyridine and 18.08 g (0.028 mol) of 1-iodo-perfluoro-n-decane were mixed and the mixture was treated by following the procedure of Example 2. Perfluoro-n-decyl-$\gamma$-methyl pyridine was distilled at 130°–132° C./6 mmHg to a total amount of 8.74 g (51.1% of theoretical value). The product, which was a colorless substance having a melting point of 50°–60° C., was found to be a 75:25 mixture of $\alpha$-$R_f$ and $\beta$-$R_f$ isomers.

COMPARISON EXAMPLE 1

In the same reaction vessel as used in Example 1, 15.82 g of pyridine and 7.83 g of trifluoromethyl iodide were mixed. The vessel was airtightly sealed and heated at 180° C. for 24 hours. After the reaction, the reactor was cooled to room temperature. Thereafter, the reaction mixture was removed from the cooled vessel and treated by following the procedure of Example 1. Consequently, there was obtained 1.17 g (19.90% of theoretical value) of trifluoromethyl pyridine. This substance was found to be a 48:41:11 mixture of $\alpha$, $\beta$ and $\gamma$ isomers.

COMPARISON EXAMPLE 2

In the same reaction vessel as used in Example 1, 18.62 g of $\beta$-methyl pyridine and 7.62 g of pentafluoroethyl iodide were mixed and the mixture was treated in the same manner as in Example 1. Pentafluoroethyl-$\beta$-methyl pyridine was distilled to a total amount of 2.02 g (30.91% of theoretical value). The substance was found to be a 39:4:19:38 mixture of 2-$R_f$, 4-$R_f$, 5-$R_f$ and 6-$R_f$ substitutes.

From the working examples and the comparison examples given above, it is evident that fluoroalkyl pyridines are obtained in higher yields when the reaction is carried out in the atmosphere of ammonia gas.

What is claimed is:

1. A method for the manufacture of a fluoroalkyl pyridine, which comprises mixing a pyridine and a fluoroalkyl iodide and subjecting the resultant mixture to a reaction by heating in the atmosphere of ammonia gas.

2. The method according to claim 1, wherein the pyridine is at least one member selected from the group consisting of pyridine, $\alpha$-methyl pyridine, $\beta$-methyl pyridine and $\gamma$-methyl pyridine and the fluoroalkyl iodide is at least one member selected from the group consisting of fluoroalkyl iodides having from one to ten carbon atoms.

3. The method according to claim 1, which comprises mixing the pyridine and the fluoroalkyl iodide at a molar ratio of 1:0.1~0.4 in the reaction vessel, then adding ammonia gas to the resultant mixture kept at temperatures in the range of from 0° C. to 5° C., sealing the reaction vessel airtightly and maintaining the reaction system at 175° C. to 190° C. for three to 24 hours.

* * * * *